US010912718B2

(12) United States Patent
Perrin et al.

(10) Patent No.: US 10,912,718 B2
(45) Date of Patent: Feb. 9, 2021

(54) MULTI-COMPOSITION COSMETIC PRODUCTS AND METHOD FOR MANUFACTURING SAME

(71) Applicant: LVMH RECHERCHE, Saint-Jean de Braye (FR)

(72) Inventors: Lily-Ann Perrin, Beaugency (FR); Valerie De La Poterie, Lailly en Val (FR)

(73) Assignee: LVMH RECHERCHE, Saint-Jean de Braye (FR)

( * ) Notice: Subject to any disclaimer, the term of this patent is extended or adjusted under 35 U.S.C. 154(b) by 0 days.

(21) Appl. No.: 15/313,026

(22) PCT Filed: May 22, 2015

(86) PCT No.: PCT/FR2015/051368
§ 371 (c)(1),
(2) Date: Nov. 21, 2016

(87) PCT Pub. No.: WO2015/177484
PCT Pub. Date: Nov. 26, 2015

(65) Prior Publication Data
US 2017/0135912 A1 May 18, 2017

(30) Foreign Application Priority Data

May 23, 2014 (FR) ..................... 14 54677

(51) Int. Cl.
| | | |
|---|---|---|
| *A61K 8/02* | (2006.01) | |
| *A45D 40/16* | (2006.01) | |
| *A61Q 1/02* | (2006.01) | |
| *A61Q 1/06* | (2006.01) | |
| *A45D 33/18* | (2006.01) | |
| *A61K 8/31* | (2006.01) | |
| *A61Q 13/00* | (2006.01) | |
| *A61Q 17/04* | (2006.01) | |
| *B29C 39/02* | (2006.01) | |
| *B29C 39/38* | (2006.01) | |
| *B29C 39/44* | (2006.01) | |
| *A61K 8/37* | (2006.01) | |
| *A61K 8/81* | (2006.01) | |
| *A61K 8/92* | (2006.01) | |
| *B29K 101/12* | (2006.01) | |
| *B29L 31/00* | (2006.01) | |

(52) U.S. Cl.
CPC ............ *A61K 8/0229* (2013.01); *A45D 33/18* (2013.01); *A45D 40/16* (2013.01); *A61K 8/0237* (2013.01); *A61K 8/31* (2013.01); *A61K 8/37* (2013.01); *A61K 8/8111* (2013.01); *A61K 8/8117* (2013.01); *A61K 8/927* (2013.01); *A61Q 1/02* (2013.01); *A61Q 1/06* (2013.01); *A61Q 13/00* (2013.01); *A61Q 17/04* (2013.01); *B29C 39/021* (2013.01); *B29C 39/38* (2013.01); *B29C 39/44* (2013.01); *A61K 2800/436* (2013.01); *A61K 2800/592* (2013.01); *A61K 2800/805* (2013.01); *B29K 2101/12* (2013.01); *B29L 2031/718* (2013.01)

(58) Field of Classification Search
CPC ............ A61K 8/0229; A61K 2800/80; B29C 39/021; A61Q 1/06; A45D 40/16
See application file for complete search history.

(56) References Cited

U.S. PATENT DOCUMENTS

| | | | |
|---|---|---|---|
| 4,291,018 A | 9/1981 | Oeda et al. | |
| 4,602,886 A | 7/1986 | Smit | |
| 4,743,443 A | 5/1988 | Pisani et al. | |
| 6,372,235 B1* | 4/2002 | Livoreil ................ | A61K 8/02 424/401 |
| 2002/0041788 A1* | 4/2002 | Look .................... | A45D 40/04 401/68 |
| 2007/0059263 A1 | 3/2007 | Taniguchi et al. | |
| 2007/0269470 A1* | 11/2007 | Takeda .................. | A61K 8/39 424/401 |
| 2013/0341833 A1* | 12/2013 | Teller ..................... | A45D 40/00 264/299 |
| 2015/0030645 A1 | 1/2015 | Pinheiro-Bairras | |

FOREIGN PATENT DOCUMENTS

| | | |
|---|---|---|
| CN | 101115461 A | 1/2008 |
| CN | 102753054 A | 10/2012 |
| CN | 107854325 A | 3/2018 |
| FR | 1396720 | 4/1965 |
| FR | 2956833 | 9/2011 |
| FR | 2958159 | 10/2011 |
| FR | 2975589 | 11/2012 |

(Continued)

OTHER PUBLICATIONS

International Search Report issued in International Application No. PCT/FR2015/051368 dated Aug. 18, 2015 (7 pages).
Written Opinion issued in International Application No. PCT/FR2015/051368 dated Aug. 18, 2015 (6 pages).
Kawanishi et al., "The Sol-Gel Transition and the Liquid-Liquid Phase Separation in Poly(vinyl chloride) Solutions", Polymer Journal, vol. 18, No. 5, p. 411-416,1986, total 6 pages.

(Continued)

*Primary Examiner* — Monica A Shin
(74) *Attorney, Agent, or Firm* — Hamre, Schumann, Mueller & Larson, P.C.

(57) ABSTRACT

The invention relates to novel multicolour, multitexture and multimaterial cosmetic products as well as to a method for hot casting cosmetic compositions containing fats, in particular an oil.
Said method advantageously renders a mold superfluous and allows the creation of products that include a plurality of compositions such as to produce highly original appearances. Said method also allows the production of products with a very irregular raised designs.

17 Claims, 1 Drawing Sheet

(56) References Cited

FOREIGN PATENT DOCUMENTS

| JP | 2002097112 A | 4/2002 |
|---|---|---|
| WO | 0191605 | 12/2001 |
| WO | 02072044 | 9/2002 |
| WO | 2011071792 A2 | 6/2011 |

OTHER PUBLICATIONS

Office Action issued for Chinese Patent Application No. 201580039766.3, dated Jan. 11, 2019, 95 pages including English translation.

* cited by examiner

MULTI-COMPOSITION COSMETIC PRODUCTS AND METHOD FOR MANUFACTURING SAME

The invention relates to novel cosmetic products comprising at least one cosmetic composition, solid at ambient temperature, containing an oil, which composition is intended to be applied to a part of the body for caring for, making up or scenting the skin or hair. The cosmetic products of the invention exhibit novel forms, novel combinations of hues and also novel combinations of textures and substances. Cosmetic products of the invention also exhibit highly original forms in the relief which it has been impossible to produce with current techniques.

The invention also relates to a novel process for hot casting of a cosmetic composition. This process consists in melting the composition in order to fluidify it and in then casting this composition in the fluid state on a surface by successive deposits of very small size which can take the form of sheets, threads or drops. The manufacturing process of the invention does not require the use of a mold, which until now has been necessary in order to manufacture cast cosmetic products.

By virtue of the process of the invention, it is possible to easily conceive of multi-composition cosmetic products, that is to say cosmetic products consisting of several different solid compositions, at the surface or in the body, which are visible or concealed. This process also makes it possible to create very fine reliefs at the surface of these products.

PRIOR ART

The solid cosmetic compositions which contain fatty substances in high proportions are generally manufactured by hot casting, either in a mold, which gives them a form, or in a dish or a pot.

Thus, the makeup articles which offer the consumer a flat surface for withdrawing the product, for example blushers, foundations or eye shadows, comprise a case with a lid and a container. These products are obtained by hot casting the liquefied product in the dish through the top or through the bottom via holes pierced in the dish. The latter is subsequently placed in the case.

Relief makeup products, such as sticks, are manufactured by molding. The composition is melted above its melting point and then cast in the mold, cooled and demolded. The demolded product is subsequently placed in a container having or not having a revolving mechanism, for the extraction or the handling thereof.

The molds are made of metal or plastic, for example of silicone, or of SEBS elastomer, for easier demolding of the objects. Manual metal molds are produced in several parts which are moved apart to make possible the demolding. Industrial metal molds are made of a part which has a slit through which compressed air ejects the stick during the demolding. These metal molds require a surface treatment, such as a spraying of a silicone oil over the walls, to facilitate the demolding and to improve the surface condition of the demolded objects.

The cosmetic product is melted above its melting point and then poured into the pattern cavities of the molds which can be preheated beforehand to a temperature of the order of 40° C. in order to prevent excessively rapid setting. The molds are cooled, once filled, by contact with a refrigerating table or in a refrigerated chamber, the temperature of which is of between −20° C. and 15° C.

The processes of the molding of sticks thus exhibit numerous disadvantages, such as the high costs of designing and manufacturing high-precision molds, the need to achieve temperatures of less than 0° C. in order to make possible the demolding, lengthy cooling times for the products which have been cast in the molds, the requirement to clean the molds after each use and the need to again heat the molds in order to carry out a new manufacturing cycle. There are other disadvantages to the use of this type of process, such as the frequent overhaul of the metal molds or the regular replacement of the silicon molds, which overhaul is rendered necessary by the repeated mechanical impacts and thermal shocks or also the impregnation of ingredients of the cosmetic compositions in the substance of the silicon molds. The lipstick sticks can exhibit alternative forms of relief and of hues but the reliefs are limited to a few tenths of a millimeter and the number of hues rarely exceeds two or three. Effects of hue have been provided but they are always geometric: of radial type (double cylinder of core-shell structure) or linear type (vertical or horizontal layers). Finally, patterns of random hues have already been provided by casting two hues in the fluid state at the same time in the mold.

The structures of core/shell sticks are obtained by molding. For example, a multicolor lipstick is manufactured by using a pair of molds: a core mold placed at the center of a cylindrical mold. A first casting of a first hue is carried out in the hollow part of the core mold, which is left to cool and solidify. After having removed the central mold, the cavity left after the removal of the core is filled with a second hue in order to obtain the multicolor lipstick. As alternative method, a separating plate can be inserted in order to create semicylindrical cavities and can then be withdrawn after solidification of the different hues. However, this method requires that the hues be subsequently rendered integral by moderate heating of their surface in order to allow them to assemble.

The structures of side by side sticks are prepared with a first mold having a semicylindrical cavity (comprising two parts, including a removable flat vertical plate). A first molten mass is poured into this cavity and cooled in order to solidify the composition. The plate is withdrawn and then replaced with a second mold identical to the first which is placed mirroring and in contact with the first composition. A second molten mass is poured into the cavity and cooled. After demolding, the two semicylindrical compositions connected together along a radial plane.

Makeup products comprising one or two patterns in relief of different hues showing from a flat surface have been provided by molding in the patent FR 2 956 833, two superimposed molds being used. A rigid flat-bottomed dish pierced with an orifice is positioned on a deformable mold. The makeup product in the liquid form is poured into the deformable mold via the orifice of the dish, so that the demolded product obtained comprises one or more patterns on the free surface provided to the consumer. The reliefs obtained have a height of the order of 1 to 2 mm.

The inventors have also attempted to carry out several castings in a mold in order to create a lipstick stick consisting of several horizontal layers of different colors. However, this process remains very limited as the minimum thickness of the layers has to be high in order to guarantee their uniformity, typically of the order of a few millimeters.

However, all these processes exhibit the disadvantage of requiring several molds, and several casting stages spaced out in time, as it is necessary to wait for the cooling and for the solidification of the first hue before casting the second, in order to prevent them from mixing.

In addition, in all the cast multihue products of the prior art, the layers of products necessarily have a flat surface as a result of gravity: either parallel to the vertical axis of the stick or perpendicular to the vertical axis of the stick, which greatly restricts the possibilities of presentation of the products which are desired to be multihue.

Finally, the molds are expensive to manufacture, in particular when it is desired to produce irregular shapes, and require frequent inspection and frequent maintenance.

The great majority of lipsticks sold are provided in the form of sticks or are cast in pots. The geometry of these products remains very symmetrical and basic. Although lipsticks have varied appearances, textures, hues and formulation properties, none of these specific features are generally encountered combined in just one and the same product.

The need thus remains to provide multicomposition cosmetic products providing novel arrangements of hue, of texture or of substance which are easier, faster and less expensive to manufacture. Another aim is to manufacture cosmetic products with a more irregular and finer relief.

OBJECTIVES OF THE INVENTION

It is desired to develop novel forms and novel presentations of solid cosmetic compositions containing an oil, in particular in a high proportion, in particular in the makeup field.

In the context of the invention, the inventors have found that it is possible to fashion such compositions according to very varied forms, reliefs and hues in order to form multihue products. They have also found a process which makes it possible to cast, during one and the same stage, cosmetic compositions of different texture in order to form multitexture products. Finally, they have found a process which makes it possible to simultaneously cast a cosmetic composition and a noncosmetic thermoplastic support material, in order to form multisubstance products.

The inventors have thus found a novel process for the hot casting of a solid composition which does not require the use of a mold or of a container, as is the case in all the processes of the prior art. This process makes it possible in particular to obtain very fine patterns, interlacings of ribbons, and also shadings of color, which have never been produced previously.

The process of the invention exhibits multiple advantages. It makes it possible to fashion products, the surface or the body of which comprises a plurality of forms and domains of different hues. The surface of these forms and these domains is not necessarily flat.

The present invention thus relates to a novel process for manufacturing a solid cosmetic product which consists in melting a composition, in casting it in the fluid state on a support according to a predefined pattern, a plurality of successive or simultaneous deposits being produced, and in then leaving them to cool.

Definitions

Within the meaning of the present invention, the term "cosmetic composition" is understood to mean the mixture of several ingredients, including an oil, forming a solid object at 25° C. The cosmetic composition is intended to be applied as is to a part of the human body for caring for, making up or scenting the skin or hair.

The term "cosmetic product" is understood to mean a product intended for sale which comprises at least one cosmetic composition optionally in combination with application means and presented in a container.

The term "multicomposition cosmetic product" is understood to mean a cosmetic product comprising at least two, preferably at least three, solid compositions which are different in the ingredients of which they are composed. All the compositions may appear different at the surface of the product and be visible by the user. Alternatively, a first composition may be located in the body of the product, with the result that the user may perceive it by the transparency of a second composition which masks it, or discover it once the second composition which masks it has been used by successive applications to the body, the face or the hair.

The term "multihue product" is understood to mean a cosmetic product comprising at least two, preferably at least three or four, cosmetic compositions having different hues.

The term "multitexture product" is understood to mean a cosmetic product comprising at least two cosmetic compositions having different textures, that is to say resulting in a different feel on being taken up or on application according to their consistency and their rheological properties. Mention may be made, as examples of textures, of water-in-oil emulsions, gels and anhydrous products.

The term "multisubstance product" is understood to mean a product comprising at least one cosmetic composition and at least one noncosmetic thermoplastic support material, which support material has been formed according to the process of the invention.

The term "solid" is understood to mean a composition exhibiting, at 25° C. and at atmospheric pressure (1 atm=$10^5$ Pa), a hardness of greater than 0.5 N, preferably of greater than 2 N, said hardness preferably being measured using a texture analyzer provided with a hemispherical probe with a diameter of 12.7 mm.

The term "solidified" is understood to mean partially or completely solidified, that is to say that a portion of the weight or the whole of the weight of the deposit is at a temperature lower than its fluidification point.

The term "thread" is understood to mean a volume, for example essentially cylindrical, the mean diameter of which is much lower than its length. The diameter is defined as the greatest dimension measured in a plane perpendicular to the length. The thread can have a mean diameter of between 0.01 mm and 5 mm, for example between 0.1 mm and 5 mm, preferably between 0.2 and 2.5 mm, more preferably between 0.2 and 1.2 mm. In one embodiment, the thread has a mean diameter of the order of 0.5 mm. The section of the thread can be circular, oval or essentially rectangular. When the section is essentially rectangular, the dimensions of the thread can be defined by its height and its width, which corresponds to the mean diameter defined above.

The term "drop" is understood to mean an essentially spherical volume with a mean diameter of between 0.01 and 5 mm, for example between 0.1 mm and 5 mm, preferably between 0.1 and 1 mm.

The term "sheet" is understood to mean an essentially parallelepipedal volume, the width of which is much greater than its thickness.

The term "fluidification point" is understood to mean the temperature at which at least a portion of the composition solid at 25° C. changes to the liquid state. The fluidification point of the composition can be the melting point T50 at which 50% of the composition is liquid, the melting point T80 at which 80% of the composition is liquid, the melting point T90 at which 90% of the composition is liquid, the dropping point of the composition or the sol-gel transition temperature of the composition.

The term "oil" is understood to mean a fatty substance which is liquid at 15° C. The term "wax", within the meaning of the present invention, is understood to denote a compound which is solid at 25° C., which exhibits a reversible solid/liquid change in state and a melting point of greater than 30° C., The term "pasty fatty compound" denotes a noncrystalline fatty compound comprising, at a temperature of 25° C., a liquid fraction and a solid fraction.

In the present patent application, the expression expressing a range of values "range from . . . to" comprises the limits, whereas the expression expressing a range of values "of between . . . and" excludes the limits.

DESCRIPTION OF THE INVENTION

A first subject matter of the invention relates to a process for the manufacture of a cosmetic product by casting at least one composition containing an oil, having a fluidification point of between 30 and 150° C. and a mean hardness—measured at 25° C. using a texture analyzer provided with a hemispherical probe—of between 0.5 and 80 N, which process comprises the sequence of the following stages:

a) the fluidification of the composition by heating it to a fluidification temperature which is greater than its fluidification point, b) the introduction of the fluidified composition into at least one casting nozzle, c) the casting of the fluidified composition, via the nozzle, on a support, in order to form a first deposit of said composition on said support, and the relative moving—in at least one of the three directions in space—of the nozzle with respect to said support, which deposit essentially retains its form after solidification, d) the halting of the casting, e) the relative displacement of the nozzle with respect to the support.

In this process, the deposit advantageously exhibits the form of drops or threads.

The process can additionally comprise a stage f).

Stage f) can consist of the repetition of stages a) to e)—at least once—in order to form at least one other deposit on said support, using a first composition or a second composition, which second composition contains an oil, which has a fluidification point of between 30 and 150° C. and which has a mean hardness—measured at 25° C. using a texture analyzer provided with a hemispherical probe—of between 0.5 and 80 N.

Stage f) can consist of the repetition of stages a) to e)—at least once—in order to form at least one other deposit on said support, using another composition.

Stage f) can consist of the repetition of stages c) to e)—at least once—in order to form at least one other deposit on said support, using the same composition. This is because, in this case, it is not necessary to repeat stage a) of fluidification of the composition or stage b) of introduction of the composition into the casting nozzle. It is possible to prepare, before starting the process of the invention, in a fluidification vessel, a volume of fluidified composition corresponding to the volume of all the deposits of composition which will be necessary to manufacture the cosmetic product in its entirety. On the contrary, it may be decided to fluidity on going along the amount of composition corresponding to just one deposit.

According to one embodiment, a subject matter of the invention is a process for the manufacture of a cosmetic product by casting at least one composition containing an oil, having a fluidification point of between 30 and 150° C. and a mean hardness—measured at 25° C. using a texture analyzer provided with a hemispherical probe—of between 0.5 and 80 N, which process comprises the sequence of the following stages:

a) the fluidification of the composition by heating it to a fluidification temperature which is greater than its fluidification point, b) the introduction of the fluidified composition into at least one casting nozzle, c) the casting of the fluidified composition, via the nozzle, on a support, in order to form a first deposit of said composition on said support, and the relative moving—in at least one of the three directions in space—of the nozzle with respect to said support, which deposit essentially retains its form after solidification, d) the halting of the casting, e) the relative displacement of the nozzle with respect to the support, and f) the repetition of stages a) to e) at least once in order to form at least one other deposit on said support, using the same composition or another composition which contains an oil, which has a fluidification point of between 30 and 150° C. and which has a mean hardness—measured at 25° C. using a texture analyzer provided with a hemispherical probe—of between 0.5 and 80 N.

According to one of its aspects, the invention relates to a casting process for the manufacture of a cosmetic product, without the use of a mold, which process comprises the sequence of the following stages:

a) the fluidification of at least one composition containing an oil, having a fluidification point of between 30 and 150° C., and a mean hardness—measured at 25° C. using a texture analyzer provided with a hemispherical probe—of between 0.5 and 80 N, by heating it to a fluidification temperature which is greater than its fluidification point, b) the introduction of the fluidified composition into a casting nozzle, c1) the casting by ejection of the fluidified composition through an orifice of the nozzle in order to obtain a volume, which volume is deposited on a support and forms, after cooling to 25° C., a first deposit of said composition on the support, c2) the relative moving—in at least one of the three directions in space—of the nozzle with respect to said support, d) the halting of the casting, then optionally e) the relative displacement of the nozzle with respect to the support, and f) the repetition of stages a) to e) at least once in order to form at least one other deposit on said support, using the same composition or another composition which contains an oil, which has a fluidification point of between 30 and 150° C., and which has a mean hardness—measured at 25° C. using a texture analyzer provided with a hemispherical probe—of between 0.5 and 80 N.

The volume of composition once deposited on the support forms a deposit which partially or completely solidifies. The ejected volume, the casting flow rate, the casting temperature and the temperature of the support can be chosen so that the deposit has essentially the same form as the volume. It is preferably desired for the form of the ejected volume to be identical to the form of the solid deposit, in the absence of mechanical or thermal stress applied to the deposit after casting.

The deposit may have a different form from the ejected volume, in particular of application of a thermal stress, for example by heating the support to a temperature of greater than 25° C. The deposit may have a different form from the ejected volume, in particular by application of a mechanical stress, for example by depositing a second deposit on a first deposit, before solidification of the first, by applying a pressure targeted at deforming the first deposit. It is preferable for the deposit to retain the form of the volume obtained at the outlet of the nozzle. In the process of the invention, the support does not act as container for the volume of fluidified composition during the cooling thereof, with the result that the solid deposit gets its form essentially from the orifice of the nozzle, in the absence of any mechanical or thermal stress applied subsequent to the casting.

In one embodiment, the form of the ejected volume is identical to the form of the solid deposit, in particular in the absence of mechanical or thermal stress applied to the deposit after casting. Thus, the mean diameter of the deposit can be equal to the diameter of the orifice of the nozzle.

The casting temperature will be defined as the temperature of the space defined between the outlet of the nozzle and the support. This space may be a thermostatically-controlled chamber. The casting temperature is preferably less than or equal to the fluidification temperature.

The process of the invention exhibits the advantage of being able to conceive of novel cosmetic products within shorter development times. This is because the cast composition flow rate can advantageously be less than that of the hot casting processes of the prior art, so as to dispense with the cooling stage necessary between two stages of casting two different compositions. The casting of the process of the invention can be carried out under virtually continuous conditions.

Once the cast composition has been deposited on the support, the deposit has a surface in contact with the support, a free surface, and optionally a surface in contact with a deposit which has been cast previously. The casting process of the invention advantageously makes it possible to create a deposit, one of the surfaces of which is nonplanar. The free surface of the deposit is preferably nonplanar.

When the support defines a hollow volume, the deposits produced according to the process of the invention exhibit the advantage of not filling this volume, in contrast to the casting processes of the prior art, which use a mold as support.

The composition deposit, once solidified, exhibits the distinguishing feature of having at least one of its three dimensions less than 5 mm, preferably of between 0.01 mm and 3 mm. Consequently, the deposit can be in the form of a cylinder (or thread), of a sphere (or drop) or of a sheet at the outlet of the nozzle. The length of a cast deposit according to the process of the invention, when it is in the form of a thread, can be greater than 1 cm, for example of between 4 cm and 2 m, for a mean diameter of 1 mm.

Stage a) of the process of the invention consists of the fluidification of the composition by heating it to a fluidification temperature which is greater than its fluidification point.

During stage a), the composition is rendered fluid by contributing heat, starting from its state which is solid at 25° C.

According to one embodiment, in a stage prior to stage a), the ingredients used for the preparation of the composition, including the oil, are mixed under hot conditions and then the mixture obtained and cooled and optionally stored for the purpose of its use in stage a).

It is also possible to prepare, in a first stage prior to stage a), a base consisting of all the ingredients used in the preparation of the composition, with the exception of the coloring substances, such as the pigments, the pearlescent agents and the dyes, and then, in a second stage prior to stage a), to add the coloring substances which will have been chosen by the consumer.

The fluid mass resulting from one of these two alternative forms is preferably kept continuously stirred in a mixer, at a constant temperature, preferably at the fluidification temperature, which is greater than the fluidification point of the composition.

The composition can be mixed, for example in a screw extruder, before being introduced into the casting nozzle. According to an alternative form, the composition can be introduced in the form of a solid powder into a screw extruder having a heating means which brings the composition to the fluidification temperature in order to bring about the fluidification thereof. The end of the extruder delivering the fluid mass of composition is advantageously connected to a means for feeding the casting nozzle.

The composition is advantageously adapted in order for—at the casting temperature—its viscosity to allow it to flow in the form of a uniform deposit on the support and in order for the deposit formed to solidify according to the kinetics desired as a function of the result expected. It is possible to wish for the deposit to solidify very rapidly or, on the contrary, slowly, in order to facilitate its adhesion to a subsequent deposit. The rate of solidification of the free surface can be adjusted by thermostatically controlling the ambient air. In one embodiment, the solidification of the free surface of the deposits is advantageously carried out in a few seconds at ambient temperature (25° C.). The deposit may exhibit the advantage of solidifying in a few seconds, with the result that it is not necessary to show a halt between two series of stages a) to e).

The characteristics of the cosmetic composition which will be described hereinafter also apply to the second and third subject matters of the invention.

The fluidification point of the composition is preferably of between 30 and 100° C., preferably between 40 and 95° C.

According to the nature of the composition and of the compounds used to structure the oil which it includes, it is possible to define the fluidification point of the composition as being the melting temperature at which a portion or all of its mass is in the liquid state. For example, the temperature TX is the temperature at which X % of the composition is in the liquid state, X being a number of between 1 and 100. It is preferable to use, in the context of the present invention, the parameters T50, T90 and T95, the temperature T50 being the temperature at which 50% of the composition is in the liquid state, the temperature T90 being the temperature at which 90% of the composition is in the liquid state and the temperature T95 being the temperature at which 95% of the composition is in the liquid state. These temperatures can be measured using a differential scanning calorimeter (DSC), such as the calorimeter sold under the name DSC 30 by Mettler, with a rise in temperature of 5 or 10° C. per minute. The curve representing the energy absorbed by the sample in order to melt as a function of the temperature (thermogram) defines an area. TX represents the temperature at which the value of the area under the curve as TX is equal to X % of the total area under the curve.

The total enthalpy of fusion of the composition is equal to the area under the curve of its thermogram obtained using a differential scanning calorimeter, such as the calorimeter sold under the name MDSC 2920 by TA Instruments, with a rise in temperature of 5 or 10° C. per minute. The enthalpy of fusion of the composition, expressed in J/g, represents the amount of energy necessary to change the composition from the solid state to the liquid state.

Thus, the enthalpy of fusion consumed at X° C. is the amount of energy absorbed by the sample in order to change from the solid state to the state which it exhibits at X° C., consisting of a liquid fraction and of a solid fraction.

The liquid fraction of the composition measured at X° C. is equal to the ratio of the enthalpy of fusion consumed at X° C. to the total enthalpy of fusion of the composition.

It is also possible to define the fluidification point as being the dropping point of the composition. The dropping point can be measured with an apparatus having standardized cups with an orifice diameter of 2.8 mm, a rate of heating of 1.0° C. or 2.0° C./min, a starting temperature 20° C. lower than the expected dropping point and an end temperature from 10 to 15° C. greater than the expected dropping point being adopted. The drop can be detected visually using a camera incorporated in the apparatus or by a measurement cell. The apparatus remembers the temperature at which the drop has flowed into a collecting sleeve.

The apparatus can be the Mettler Thermosystem FP900 model combined with a Mettler FP83HT measurement cell, or the Toledo DP70 model. The composition is hot cast in the cup, then cooled and maintained in a chamber at 20° C. for four hours.

It is also possible to define the fluidification point as being the sol-gel transition temperature of the composition, as defined, for example, in the document *Polymer Journal*, 18 (5), 411-416 (1986).

It is also possible to define the fluidification point as being the softening point of the composition. For example, the softening point measured according to this method can be of between 55 and 85° C.

In order to measure the softening point of the composition by the ring and ball method, a brass ring of defined dimensions is filled with molten composition and placed on a support. A steel ball (diameter=9.53 mm, weight=3.5 g) is on the composition at the center of the ring. The support carrying the filled ring is subsequently immersed in a beaker (at least with an internal diameter of 85 mm and a height of more than 120 mm) containing demineralized water, glycerol or a silicon oil, according to the temperature range which it is desired to scan. The temperature of the bath is increased by 5° C.min$^{-1}$. The temperature at which the substance surrounding the ball frees itself from the ring and falls onto the lower plate of the support is recorded.

The composition used in the context of the invention preferably has a dropping point of greater than 50° C., for example of between 70 and 85° C. The dropping point of the composition can be greater than 50° C., preferably greater than 55° C., for example of between 55 and 60° C., of between 70 and 80° C., or between 75 and 85° C.

The composition can have a temperature T50 of between 40 and 70° C., for example between 55 and 60° C. The composition can correspond to a T90 of between 70 and 85° C., more specifically between 75 and 80° C.

The fluidification temperature is preferably greater by 1 to 15° C., for example greater by 5 to 10° C., than the fluidification point of the composition, so as to obtain the fluidified composition in a highly homogeneous form, in particular in the case where it contains waxes or pulverulent substances, such as pigments or fillers, in a relatively high amount The composition fluidified at the fluidification temperature is advantageously introduced into the casting nozzle by applying a pressure ranging from 100 to 4000 kPa, for example from 500 to 2500 kPa.

In order to prevent any obstruction of the feed means connecting the vessel and the nozzle, it will be possible to encase them in jacketed hot water devices in order to keep the composition in these feed means at the desired fluidification temperature.

The fluidified composition can be dispensed by nozzles or other dispensing parts. Once cooled, it forms a deposit having an appropriate hardness at 25° C. At the casting temperature, the fluidified composition exhibits a viscosity which is sufficiently low to be dispersed through an orifice of the nozzle and to make it possible to deposit thin sheets, threads or drops. The composition preferably exhibits, at the time of its deposition on the support, a sufficiently high viscosity and/or cooling kinetics such that the deposit retains its form until it solidifies. It will be possible to choose compositions having a low viscosity to produce more distinct deposits, the thickness of the sheets, the mean diameter of the threads and the mean diameter of the drops being reduced in particular.

In certain applications, the composition advantageously has a high rate of dissipation of the heat, so that the composition deposit rapidly solidifies. It will be possible to modulate these heat dissipations by modifying the temperature of the support and/or by placing the support in a thermostatically controlled chamber.

The casting temperature of the composition in the nozzle in stage b) can be less than or equal to the fluidification temperature. It remains greater than or equal to the fluidification point of the composition.

The solidification of the surface of a composition deposit is carried out in a few seconds when the support and the atmosphere which surrounds it are at 25° C. It is possible to decide to accelerate the solidification of the deposit by using a casting chamber thermostatically controlled at a temperature of less than 25° C., for example equal to 10° C., 4° C. or 0° C.

The casting temperature is, for example, of between 30 and 110° C., in particular between 40 and 90° C.

The casting temperature can be less than or equal to the fluidification temperature. This is because the fluidification temperature makes it possible to melt the composition at a temperature where it is sufficiently fluid to be very homogeneous. At the time of the casting, it is possible to lower the temperature of the composition in order to give it more consistency, in order for the deposit formed on the support after passing the composition through the nozzle to obtain essentially the form which results directly from its passage through the orifice of the nozzle. It is preferable for the deposit not to flow under its own weight until complete solidification and cooling at ambient temperature, at a temperature of between 20 and 25° C. The deposit can nevertheless be deformed, once it is in contact with the support and before complete solidification, by subsequent application of another deposit coming into contact with it.

The casting temperature will be adapted as a function of the rate of cooling of the composition but also as a function of the viscosity of the fluidified composition in order to be appropriate to a uniform flow through the nozzle. A composition deposit completely solidifies preferably in a period of time of between a few seconds and a few minutes.

In one embodiment, the casting temperature is less than or equal to the fluidification temperature and fairly close to the fluidification point, so that the deposit or deposits formed cool rapidly and solidify rapidly. In particular, the deposits do not spread out over the support before being solidified.

For example, the casting temperature is greater by at most 30° C., preferably by at most 20° C., than the fluidification point of the composition and lower by at least 10° C. than the fluidification temperature of the composition.

It is also possible to vary the temperature of the support in order to modulate the rate of solidification of the deposits. Thus, in one embodiment, the temperature of the support is less than or equal to the casting temperature of the composition; for example, the temperature of the support is of the order of 20 to 25° C. In another embodiment, the temperature of the support can be between 25° C. and 50° C., in order to provide good adhesion between the support and the deposit, or between the deposits with each other.

The dynamic viscosity of the composition, at the casting temperature and at atmospheric pressure, is preferably of between 1 and 10 000 mPa·s, for example between 100 and 500 mPa·s.

According to one embodiment, the dynamic viscosity of the composition at the casting temperature is preferably of between 1 and 10 000 mPa·s, for example between 100 and 500 mPa·s, or between 10 and 15 mPa·s.

The viscosity of the composition can be measured with a Mettler RM 180 viscometer (Rheomat) can be equipped with different axes as a function of the order of magnitude of the viscosity which it is desired to measure. For a viscosity ranging from 180 mPa·s to 4020 mPa·s, the instrument is equipped with a spindle 3. For a viscosity ranging from 1 Pa·s to 24 Pa·s, the instrument is equipped with a spindle 4 and, for a viscosity ranging from 8 Pa·s to 122 Pa·s, the instrument is equipped with a spindle 5. The viscosity is read on the instrument in deflection units (AU). Reference is then made to tables supplied with the measurement instrument, in order to obtain the corresponding value in poises. The rate at which the spindle rotates is 200 revolutions per minute. From this moment, when the spindle is set rotating, to an unvarying applied speed of rotation (in the case in point, 200 revolutions per minute). The value of the viscosity can vary over time. The measurements are thus taken at regular intervals until they become unvarying. The value of the viscosity which has become unvarying over time is the value selected as being the value of the dynamic viscosity of the composition.

It will be possible to attempt to optimize at least one of the five following parameters of the process of the invention: the nozzle diameter, the distance between the nozzle and the support, the speed of the movements of the support, the speed of the movements of the nozzle, the fluidified composition flow rate at the outlet of the nozzle and the fluidified composition temperature at the outlet of the nozzle.

The inventors have found that these five parameters make it possible, for a given composition, to guarantee a uniform form of the deposits, good adhesion of the deposits to one another and a superimposition of the deposits which does not generate deformations after the casting.

The nozzle has in the lower part an orifice which makes possible the flow of the fluidified composition. One of the dimensions of this orifice ranges from 0.01 to 5 mm. It ranges, for example, from 0.05 to 3 mm, from 0.1 to 1.5 mm or from 0.3 to 0.8 mm.

The orifice can have any form. The form is preferably circular. According to one embodiment, the orifice defines a disk with a diameter of 0.1 mm to 1 mm.

A person skilled in the art will know how to adapt the distance of the nozzle with respect to the support and the flow rate of the composition through the nozzle so as to retain the integrity of the composition stream through the nozzle and to make possible rapid cooling of the deposit during the casting.

If the distance between the nozzle and the support is too small, the geometry of the deposits will be nonuniform. If the distance between the nozzle and the support is too great, there is a risk of the volume of fluidified composition exiting from the nozzle deforming and/or solidifying before being deposited on the support.

By choosing a distance between the nozzle and support which is less than the diameter of the nozzle, it is possible to produce composition deposits having different thicknesses with the same nozzle, in so far as, in this case, the nozzle acts as a scraper. By varying the casting flow rate at a given scraping height, it will also be possible to vary the width of the deposit.

The deposit generally retains the form which the fluidified composition had at the nozzle outlet but it can nevertheless be deformed, once it is in contact with the support and before complete solidification, by subsequent application of another deposit coming into contact with it, in particular when the distance between the nozzle and the support is less than the diameter of the nozzle.

In the case where it is desired to superimpose several deposits, it will be possible to attempt to control their adhesion in order to guarantee the cohesion of the cast cosmetic product. The optimum adhesion between two deposits can depend essentially on the viscosity and/or on the percentage of liquid fraction mentioned above of the composition at the casting temperature. The optimum adhesion between two deposits can also depend on the surface of the contact region between two deposits. This surface can be modulated as a function of the distance between the nozzle and the support and/or of the casting temperature.

It will be possible to attempt to adapt the relative rate of displacement between the nozzle and the support. This is because, if it is too high, there is a risk of the deposits being noncontiguous and/or of having a diameter less than that of the nozzle, which it is preferable to avoid as this would introduce defects into the cast product.

The relative rate of displacement of the nozzle with respect to the support during the casting can range from 0 to 300 mm/s, for example from 100 to 150 mm/s.

For deposits of very small volume, such as drops, the nozzle is preferably immobile with respect to the support at the moment of the ejection of the drop by the nozzle.

For the deposits in the thread form, the rate of displacement of the nozzle and the casting flow rate will be chosen as a function of the effect desired but also of the viscosity of the composition at the casting temperature.

The flow rate and the temperature of casting are advantageously adapted as a function of the nozzle diameter chosen, so that the deposit solidifies very rapidly after the casting of the composition.

The fluidified composition is cast at a controlled flow rate, from a casting nozzle, on the support, preferably according to a predetermined pattern. The deposits—which have been produced by the repetition of casting cycles comprising stages a) to e)—solidify and advantageously adhere to one another to form the product of the invention in relief and/or comprising a plurality of hues.

The flow rate is, for example, of between 0.05 and 2 mm$^3$/s for a nozzle with a diameter of 0.1-1 mm. The casting flow rate can be of between 0.1 and 1 mm$^3$/s.

The flow rate is controlled so that a first deposit of at least one first composition is partially solidified before a second deposit is cast in contact with the first.

The flow rate can also be adapted as a function of the relative rate of displacement of the nozzle with respect to the support.

The temperature of the fluidified composition at the outlet of the nozzle, also known as casting temperature, can be chosen so as to obtain a relatively low viscosity for good extrusion of the substance and a sufficiently high viscosity in order to obtain a deposit of uniform form throughout the duration of the casting at the nozzle outlet.

The process can comprise the casting of several deposits through several nozzles concomitantly. The simultaneous castings are in this case preferably carried out at different coordinates of the support. The nozzles can be integral with one another and move according to parallel trajectories or, on the contrary, may each have their own displacement means, so as to follow trajectories independent of one another.

The process can also comprise the casting of a composition deposit and the casting of a thermoplastic material deposit, concomitantly or separately.

The process of the invention can comprise a stage g) of casting a thermoplastic substance. This stage can be carried out prior to, subsequent to or simultaneously with stage c) of casting the cosmetic composition.

The thermoplastic substance can, for example, be chosen from the following: polyethylene (PE), polyvinyl chloride (PVC), polypropylene (PP), polystyrene (PS), polymethyl methacrylate (PMMA), polyethylene terephthalate (PET), polylactic acid (PLA), polyamide (PA), acrylonitrile/butadiene/styrene (ABS), and also the copolymers of the above.

A thermoplastic material can be cast at the same time as the cosmetic composition but using another nozzle. In this embodiment, the choice will preferably be made of deposits in the form of drops of 0.4 to 0.7 mm, making it possible in particular to produce very fine shadings.

The support advantageously defines a surface on which the composition deposits or deposits are cast. The surface is essentially flat in the sense that its radius of curvature is low (less than 20°)(. This surface does not define a volume which the composition deposit will fill. The support does not perform the function of mold, in contrast to the supports used in the prior art, in particular for the manufacture of lipsticks as a stick and in a dish.

The support can be of cosmetic or noncosmetic nature.

The temperature of the support can be less than or equal to 25° C., for example equal to 10° C., 4° C., or 0° C., in the case where it is desired to accelerate the cooling of the cast composition deposit. With the opposite objective, it is possible to heat the support to a temperature of greater than 25° C.

According to a preferred embodiment, the support is of cosmetic nature and can be applied to the skin in the same way as the composition which was cast above. The support can be a lipstick, a scenting product, a solid foundation or an eye shadow.

For example, the support is a cosmetic product which was manufactured by molding or pressing prior to the implementation of the process of the invention. In this embodiment, the support can be produced by melting a mixture predominantly comprising a fatty phase which is solid at 25° C., by casting said mixture in a mold, by cooling said mixture and by then demolding the part thus formed.

The invention exhibits the advantage of making possible the assembling of several cosmetic products which are formed independently.

The product of the invention can comprise the assembling of an anhydrous cosmetic support and anhydrous deposits, of an anhydrous support and water-in-oil emulsion deposits, of a water-in-oil emulsion support and anhydrous deposits, or of a water-in-oil emulsion support and water-in-oil emulsion deposits.

The support of noncosmetic nature can be a part made of metal or plastic. It can also constitute a container acting as packaging for the cosmetic product.

The support can remain integral with the cosmetic product obtained on completion of stage f) or, on the contrary, be separated therefrom. The support is thus intended to be separated from the cosmetic product or, on the contrary, constitutes a part of the cosmetic product of the invention.

Stage f) can be carried out several times. This is because stages a) to e) can be repeated one or more times so as to form several deposits on the support. These deposits can be in contact with one another or, on the contrary, be deposited in unconnected fashion on the support. For this, the nozzle is displaced in a plane parallel to the mean plane of the support or in a plane perpendicular to the latter.

According to the process of the invention, the composition and the diameter of the nozzle are chosen so that it is not necessary to wait for a first deposit to be partially or completely solidified before producing a second deposit. On the contrary, it is preferable for the first deposit not to be solidified when a second deposit is cast and comes into contact with the latter, so as to promote their adhesion.

The composition used in the context of the casting process of the invention is solid at 25° C. and contains at least one oil. The oil or the mixture of oils is preferably the predominant compound of the composition.

The composition preferably has a fluidification point of between 30 and 150° C., and a mean hardness—measured at 25° C. using a texture analyzer provided with a hemispherical probe—of between 0.5 and 80 N.

This composition makes it possible to produce deposits, in particular deposits exhibiting a very low thickness, because it has a sufficient fluidity and a sufficiently high consistency for the deposit not to be deformed after passing through the orifice of the nozzle, for the deposit not to subside once cast on the support before being solidified, and for the deposit to adhere to the support or to a deposit produced beforehand.

For example, the hardness of the composition—measured according to one of the methods described hereinafter—is of between 0.5 and 80 N, preferably of between 2 and 70 N, more preferably of between 3 and 45 N. The hardness of the composition can be, for example, of between 18 and 44 N, or between 30 and 40 N. In certain embodiments, the hardness of the composition is between 15 and 25 N, between 6 and 17 N or between 9 and 15 N.

The hardness of the compositions can be measured with a texture analyzer from Stable Micro Systems, model TA.XT.Plus, by penetration of a hemispherical probe with a diameter of 12.7 mm. The measurement was carried out in a Cleopatra pot which was filled with 100 ml of composition. The mean of three measurements carried out on three different samples is preferably taken, the following measurement parameters being chosen: approach at 2 mm/s, measurement at 2 mm/s, withdrawal at 2 mm/s, penetration at 13 mm, relaxation of 25 sec, and triggering force at 0.02 N.

The hardness of the composition can also be measured with a TA-XT2i texture analyzer from Rheo, equipped with an ebonite cylinder with a height of 25 mm and a diameter of 8 mm. The hardness measurement can be carried out at the center of five composition samples. The cylinder is introduced into each composition sample at a prerate of 2 mm/s, then at a rate of 0.5 mm/s and finally at a withdrawal rate of 2 mm/s. The total displacement is 1 mm.

The composition can correspond to the following parameters:
- a hardness of between 15 and 25 N and a dropping point of between 70 and 80° C., or
- a hardness of between 6 and 17 N and a dropping point of between 75 and 85° C., or
- a hardness of between 9 and 15 N and a dropping point of between 55 and 60° C., or
- a hardness of between 18 and 44 N, a dropping point of between 40 and 70° C., a temperature T50 of between 70 and 85° C., and a temperature T90 of between 74 and 81° C., or
- a hardness of between 30 and 40 N, a dropping point of between 55 and 60° C., a temperature T50 of between 75 and 80° C., and a temperature T90 of between 75 and 80° C.,
- a hardness between 40 and 45 N and a dropping point of between 75 and 80° C.

The process of the invention can comprise treatments which are carried out during one of stages a) to f), or in a separate stage, in order to improve the esthetic quality of the product. It is possible, for example, to carry out an infrared flame treatment of the deposits successively produced by the process in order to smooth the surfaces created by the juxtaposition thereof, the superimposition thereof or the overlapping thereof.

Other surface treatments known in the state of the art, such as the creation of patterns by a laser, the spraying of pearlescent agents or also the electrodeposition of pearlescent agents, can be envisaged.

The invention also relates to a cosmetic product obtained by melting a solid composition at 25° C. containing an oil and by at least one deposit of said composition in the fluid state, said deposit having the form of a sheet, of a thread or of a drop. It is possible to provide for the product to comprise several deposits of different forms.

A second subject matter of the invention is a multihue, multitexture or multisubstance cosmetic product, in particular a makeup product, a care product, a sun protection product or a scenting product, comprising at least one deposit on a support of a solid cosmetic composition containing at least one oil which preferably has a fluidification point of between 30 and 150° C., and which has a mean hardness—measured at 25° C. using a texture analyzer provided with a hemispherical probe—of between 0.5 and 80 N, the deposit having the form of threads and/or of drops with a thickness of less than 5 mm.

The product preferably comprises at least two deposits of a cosmetic composition. It can also comprise several deposits of different cosmetic compositions.

A third subject matter of the invention is a multihue, multitexture or multisubstance cosmetic product, in particular a makeup product, a care product, a sun protection product or a scenting product, comprising a plurality of domains consisting of different cosmetic compositions, which are solid at 25° C. each containing, independently of one another, at least one oil, the compositions having, independently of one another, a fluidification point of between 30 and 150° C., and a mean hardness—measured at 25° C. using a texture analyzer provided with a hemispherical probe—of between 0.5 and 80 N, the product comprising neither a stack of flat layers parallel to one another, nor a succession of coaxial cylindrical layers, nor a flat cosmetic surface. The term "flat cosmetic surface" is understood to mean at least one free surface of a cosmetic composition of the product of the invention which a user can remove.

The description of the product which follows applies, if appropriate, to the second subject matter and to the third subject matter of the invention.

According to one of its aspects, the cosmetic product of the invention comprises a plurality of domains of compositions in contact with one another which have different dropping points and hardnesses. These domains can describe geometric patterns or nongeometric patterns. Their hues can be identical or different.

The product of the invention can assume highly varied forms, such as a stick, a hemisphere or a sphere.

The surface or the body of the product of the invention can, for example, exhibit nongeometric multicolor structured forms. The term "structured form" is understood to mean a pattern in two dimensions, the form of which is not random.

The product of the invention can comprise openwork forms, interlacings of ribbons, such as braids, porous surfaces or shadings of colors.

The cosmetic product of the invention can have one or more functionalities, for example be a makeup product, a care product, a sun protection product or a scenting product. Mention may be made, among the makeup products, of products for making up the lips, eyes, cheeks, eyebrows, face and body, for example a lipstick, a blusher or an eye shadow. In one embodiment, the cosmetic product of the invention can be used as eye shadow, blusher, lip gloss, lip balm, lipstick or foundation. It can also have several of these functionalities.

Another subject matter of the invention is a cosmetic product comprising a cosmetic composition, the reliefs of which have a height of less than 1 mm, preferably of less than 0.5 mm, more preferably of less than or equal to 0.1 mm, or such that its surface for presentation to the user exhibits regions of very high curvature. These patterns in relief could not be obtained previously by a conventional casting process in a mold.

The cosmetic product of the invention can comprise several compositions described above. In a specific embodiment, the product of the invention comprises the assembling i) of a stick of lipstick and ii) of at least one deposit of the same composition as the stick of lipstick, with the exception of the pearlescent agents and pigments which it contains.

The support of the cosmetic product of the invention can be a pressed powder produced one of the following series of stages: i) compacting, using a pattern cavity, a mixture comprising a predominant proportion of powders, in order to form powder cakes, ii) compacting a mixture comprising a predominant proportion of powders, and laser cutting according to the form desired, or iii) mixing powders in a solvent in order to obtain a paste, which is extruded, cutting up the paste with a hollow punch according to the form desired, and drying.

The cosmetic product of the invention comprise a packaging, such as a bottle or a case. The case can comprise a lid which can be articulated on a base, and comprise a mirror. The base can comprise a recess into which is placed an applicator, in the form of a brush, including a fine brush, or a foam tip fixed to a rod. The applicator can be housed in and snapped into the case.

The packaging can have one or more compartments or recesses. One of these compartments can contain different compositions which are in contact with one another, without it being necessary to separate them by walls. In contrast, in the prior art, each compartment is intended to receive just one composition at the same time, in view of the manufacturing constraints of the casting processes.

The characteristics of the cosmetic composition which will be described hereinafter can be applied to the first, second and third subject matters of the invention.

The cosmetic composition can be anhydrous or can contain both an aqueous phase and a fatty phase. The composition can, for example, be a water-in-oil emulsion which is solid at ambient temperature. Said composition preferably predominantly contains fatty substances, such as oils, waxes and pasty fatty compounds.

The composition used in the process of the invention or forming part of the product of the invention contains an oil, which may or not be volatile.

The volatile oils can be chosen from isododecane, isodecane, isohexadecane, octamethylcyclotetrasiloxane, decamethylcyclopentasiloxane, dodecamethylcyclohexasiloxane or pentacyclomethicone.

Mention may in particular be made, as nonvolatile hydrocarbon oil, of wheat germ, sunflower, grape seed, sesame, corn, apricot, castor, shea, avocado, olive, soybean, sweet almond, palm, rapeseed, cottonseed, hazelnut, macadamia, jojoba, alfalfa, poppy, pumpkinseed, gourd, blackcurrant, evening primrose, millet, barley, quinoa, rye, safflower, candlenut, passionflower or musk rose oil; shea butter; or also caprylic/capric acid triglycerides; synthetic ethers having from 10 to 40 carbon atoms; petrolatum, polydecenes, hydrogenated polyisobutene, polybutylenes, hydrogenated polyisobutylenes, hydrogenated polydecenes, vinylpyrrolidone copolymers, such as PVP/hexadecene copolymer, pentaerythrityl tetrapelargonate, polyglycerol-2 triisostearate, tridecyl trimellitate, triisoarachidyle citrate, pentaerythrityl tetraisononanoate, glyceryl triisostearate, pentaerythrityl tetraisostearate and glyceryl tri(2-decyltetradecanoate), squalane, synthetic esters, such as, for example, cetearyl octanoate, isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, heptanoates, octanoates, decanoates or ricinoleates of alcohols or polyalcohols, such as propylene glycol dioctanoate; hydroxylated esters, such as isostearyl lactate or diisostearyl maleate; polyol esters and pentaerythritol esters; fatty alcohols which are liquid at ambient temperature and which comprise a branched and/or unsaturated carbon-based chain having from 12 to 26 carbon atoms, such as octyldodecanol, isostearyl alcohol, oleyl alcohol, 2-hexyldecanol, 2-butyloctanol and 2-undecylpentadecanol; higher fatty acids, such as oleic acid, linoleic acid or linolenic acid; and their mixtures.

The nonvolatile silicone oils which can be used in the composition can be phenyl trimethicones or nonvolatile polydimethylsiloxanes (PDMS).

The oils can represent from 0.01 to 99% of the total weight of the composition, preferably from 0.05 to 60% and better still from 1 to 35%.

The composition can contain a structuring compound which gives the oil which it contains a solid consistency at 25° C. This structuring compound can be chosen from waxes, pasty fatty substances, oil-gelling polymers and oil-gelling inorganic compounds.

The composition can comprise a mixture of oil(s), of wax(es), of pasty fatty substance(s), of pigment(s) and of filler(s). For example, the oils represent between 55 and 65% by weight of the composition, while the waxes represent from 2 to 20% by weight of the composition and the pasty fatty substances represents from 10 to 30% by weight of the composition. Another composition will be such that the oils represent between 55 and 65% by weight of the composition, while the waxes represent from 5 to 11% by weight of the composition and the pasty fatty substances represent from 20 to 30% by weight of the composition.

The term "wax", within the meaning of the present invention, is understood to denote a solid compound at 25° C. which exhibits a reversible solid/liquid change in state and a melting point of greater than 30° C., preferably of greater than 45° C. Mention may be made of microcrystalline waxes, paraffin waxes, polyethylene waxes, ozokerite, carnauba wax, beeswax, the products comprising a mixture of polyethylene and alcohols comprising from 20 to 50 carbon atoms, silicone waxes, in particular alkyl dimethicones, $C_{20}$-$C_{40}$ alkyl stearates, the waxes obtained by catalytic hydrogenation of vegetable oils having linear or branched $C_8$-$C_{32}$ chains, such as hydrogenated jojoba oil, the waxes obtained by hydrogenation of castor oil esterified with a fatty alcohol, candelilla wax, maleic anhydride and α-olefin copolymers, the waxes obtained by metallocene catalysis and lanolin wax.

The term "pasty fatty compound" denotes a noncrystalline fatty compound comprising, at a temperature of 25° C., a liquid fraction and a solid fraction. The pasty compound is, for example, chosen from the group consisting of lanolin and its derivatives, polymeric silicone compounds, copolymers of alkyl (meth)acrylates preferably having a $C_8$-$C_{30}$ alkyl group, homo- and copolymeric oligomers of vinyl esters having $C_8$-$C_{30}$ alkyl groups, homo- and copolymeric oligomers of vinyl ethers having $C_8$-$C_{30}$ alkyl groups, liposoluble polyethers resulting from polyetherification between one or more $C_2$-$C_{50}$ diols, copolymers of ethylene oxide and/or of propylene oxide with long-chain $C_6$-$C_{30}$ alkylene oxides, diglycerol esters, arachidyl propionate, phytosterol esters, noncrosslinked polyesters resulting from the polycondensation between a linear or branched $C_4$-$C_{50}$ dicarboxylic acid or polycarboxylic acid and a diol or a polyol, the ester resulting from the esterification reaction of hydrogenated castor oil with isostearic acid, such as a mono-, di- or triisostearate of hydrogenated castor oil, a mixture of soya sterols and of oxyethylenated (5 OE)/oxypropylenated (5 OP) pentaerythritol, and their mixtures.

An oil-gelling agent is, for example, chosen from polyamides, such as polyamide copolymers comprising an ester ending (Uniclear®, Union Carbide), or else silicone polyamides, or else L-glutamide derivatives, such as dibutyl lauroyl glutamide, sold by Ajinomoto, or one of their mixtures, fumed silicas, clays, Diisostearyl Malate (and) Bis-Dioctadecylamide Dimer Dilinoleic Acid/Ethylenediamine Copolymers, such as Haimalate PAM® sold by Kokyu Alcohol Kogyo, or else hydrogenated or nonhydrogenated copolymers comprising at least one styrene unit, such as, for example, a hydrogenated styrene/methylstyrene/indene copolymer, dextrin palmitate or styrene/butylene/styrene or styrene/ethylene-propylene/styrene block (diblock, triblock, star-branched) copolymers. The composition can, for example, contain from 10 to 15% by weight of wax(es), from 0 to 10% by weight of pasty fatty substance(s) and from 60 to 70% by weight of oil(s).

The composition comprises, for example, an anhydrous gel containing an oil and an agent which gels this oil, as described in the document FR 2 958 159 or FR 2 975 589. According to one embodiment, the gelling agent is a polymer of polyamide type comprising an amide ending, preferably a polymer of polyamide type comprising a tertiary amide ending (ATPA).

Use may be made, as oil, of the mixture of a nonvolatile hydrogenated polyalkylene oil, in particular a hydrogenated polyisobutene, and a fatty acid ester comprising at least one free hydroxyl group, for example a hydroxystearate ester, preferably ethylhexyl hydroxystearate, when the gelling agent is an ATPA.

The textures of solid emulsion type are preferably emulsions, the aqueous phase of which can comprise water-miscible organic solvents, such as ethanol, isopropanol, propylene glycol, ethylene glycol, 1,3-butylene glycol, dipropylene glycol, $C_3$-$C_4$ ketones and $C_2$-$C_4$ aldehydes.

The aqueous phase (water and optionally the water-miscible organic solvent) can be present at a content ranging from 1% to 95% by weight, in particular ranging from 3% to 80% by weight and especially ranging from 5% to 60% by weight, with respect to the total weight of the composition. This aqueous phase can, if appropriate, be thickened, gelled or structured by additionally incorporating therein an aqueous gelling agent known to a person skilled in the art.

The composition can contain inorganic, organic or pearlescent pigments and optionally fillers.

Mention may be made, among inorganic pigments, by way of examples, of titanium dioxide, optionally surface-treated; black, yellow, red and brown iron oxides; manganese violet; ultramarine blue, chromium oxide; chromium oxide hydrate and ferric blue.

Mention may be made, among organic pigments, for example, of the pigments D & C Red No. 19; D & C Red No. 9; D & C Red No. 21; D & C Orange No. 4; D & C Orange No. 5; D & C Red No. 27; D & C Red No. 13; D & C Red No. 7; D & C Red No. 6; D & C Yellow No. 5; D & C Red No. 36; D & C Orange No. 10; D & C Yellow No. 6; D & C Red No. 30; D & C Red No. 3; carbon black and lakes based on cochineal carmine.

The pearlescent pigments can be chosen in particular from white pearlescent pigments, such as mica covered with titanium oxide or bismuth oxychloride, and colored pearlescent pigments, such as titanium oxide-coated mica with iron oxides, titanium oxide-coated mica with ferric blue or chromium oxide, or titanium oxide-coated mica with an organic pigment of the abovementioned type, and also pigments based on bismuth oxychloride.

The fillers can be chosen from talc, a magnesium silicate hydrate; micas having dimensions of 2 to 200 µm; kaolin, an aluminum silicate hydrate; zinc and titanium oxides; calcium carbonate, magnesium carbonate and basic magnesium carbonate; silica; zinc stearate, magnesium stearate, lithium stearate, zinc laurate or magnesium myristate; powders formed of synthetic polymers, such as polyethylene, polyesters and polyamides (for example nylon); spherical silica; spherical titanium dioxides; glass and ceramic beads; powders formed of organic materials of natural origin, such as corn, wheat or rice starches, which may or may not be crosslinked; powders formed of synthetic polymers which may or may not be crosslinked and which are spheronized, such as powders formed of polyamide, such as poly-β-alanine powders and nylon powders, powders formed of polyacrylic or polymethacrylic acids, polystyrene powders crosslinked by divinylbenzene, silicone resin powders or Teflon powders.

The composition can contain a cosmetic active principle chosen from vitamins A, E, C and B3, provitamins, such as D-panthenol, tocopherol phosphate, soothing active principles, such as α-bisabolol, aloe vera or allantoin, restructuring agents, menthol, honey, emollients, moisturizing agents, antiwrinkle active principles, plumping and tightening active principles and their mixtures.

The composition can comprise other ingredients commonly used in cosmetic compositions. Such ingredients can be chosen from antioxidants, fragrances, essential oils, preservatives, cosmetic active principles, moisturizers, sunscreens, surfactants, emulsifiers, dispersing agents, antifoaming agents, neutralizing agents, stabilizing agents and their mixtures.

The invention covers the cosmetic products, in particular the cosmetic products for making up the skin, obtained according to the process described above.

The composition deposit or the sequence of composition deposits are advantageously produced by virtue of numerical control means. In this case, the casting nozzle or nozzles are connected are controlled by software which makes it possible to program the spatial and temporal coordinates of the deposits.

The casting of the composition on the support can be carried out according to a pre-existing model which is found in the form of a digital file. In one embodiment of the invention, the drawing in two or in three dimensions of the cosmetic product which it is desired to manufacture is produced prior to the casting of the composition. This drawing advantageously takes the form of a digital file which can be converted into coordinates for successive deposits.

In one embodiment, an object is created using modeling software in the form of a digital file. This file can represent a meshing and be in an .STL or .OBJ format. However, other formats can contain more information on the object, such as the colors and the materials on which it is composed. The digital file can be composed of a polygonal shell (or meshing) representing the digital virtual object.

The digital file can subsequently be opened in a G-code editor. G-code is a digital programming language which allows the motors of the device to be controlled. The digital file for representing the model to be reproduced can be converted into G-code using software known to a person skilled in the art. The G-code contains all the information relating to the coordinates and the sequence of the movements of the support and of the casting nozzle.

Thus, in a specific embodiment of the invention, the process employs a motorized support, a motorized casting nozzle, a means for feeding with fluidified cosmetic composition, stepper motors, a control board, software which makes it possible to convert a digital object into G-Code and software appropriate for transmitting the G-code to the control board.

The process of the invention thus makes it possible to reproducibly produce identical forms which are in accordance with a model in two or three dimensions.

The casting nozzle is preferably used in combination with a means for feeding with composition. This means can be a syringe provided with a motorized piston, a screw or a pressure differential. This feeding means can also make it possible to regulate the casting flow rate of the composition.

In one embodiment, the feeding means chosen is a syringe; the piston of the syringe is coupled to a screw-nut-gears system fed by a stepper motor. When the motor turns in one direction, the piston forces the substance out of the tip of the syringe and, when it turns in the opposite direction, the piston comes back up and retains the substance in order to prevent it from flowing under gravity when the casting is halted.

The device or the nozzle advantageously have means for controlling the flow rate of the fluidified composition exiting from the nozzle.

The device can thus comprise a control unit used to actuate motors which make it possible to move the nozzle and/or the support in at least two of the three directions in space.

The device used for the implementation of the process of the invention comprises at least one casting nozzle having an opening or orifice, which nozzle is connected to mechanical means and motors which make it possible to displace it in the three directions in space.

The mechanical means are driven by the motors in order to displace the nozzle and the support, along an advantageously predetermined path, during the casting stage c) or after the halting of the casting in stage d), in order to displace the nozzle to another point of the support and to produce a fresh deposit, or to use another nozzle in order to cast another composition at the same point.

According to one embodiment, the nozzle is driven in a vertical movement (Z axis) and the support is displaced on rails along a horizontal path (Y axis and X axis).

The movements can be carried out in the three directions in space at the time of the casting but also once the flow has been withdrawn, in order to obtain the form or the spatial arrangement of substances and/or hues desired.

These mechanical movements are preferably obtained by control signals sent by a CAD/CAM (computer/controller) system. In such a system, the cosmetic product is designed on a computer and then software converts the three-dimensional form into a data stream. These data are transmitted to the drive motors in the form of control signals via a computer-aided control device.

Several heating means are used to keep the composition described above in the fluid state, at the fluidification temperature and at the casting temperature.

The device can optionally comprise at least one means for controlling the temperature of the support, one means for controlling the temperature of the composition and/or one means for controlling the temperature of the atmosphere, so as to modulate the rate of solidification of the composition deposit. The modulation of this rate can be the acceleration or the slowing down and can make it possible, for example, for a first deposit to adhere to a second deposit which will be produced subsequently, before the first deposit has completely solidified.

During stage a) of the process of the invention, the composition is fluidified by heating to a fluidification temperature greater than or equal to its fluidification point. The device used in the context of the process thus comprises a heating device upstream of the casting nozzle in order to liquefy the composition. This heating means is advantageously used in combination with a vessel which keeps the fluidified composition stirred at an unvarying temperature.

During stage b) of the process of the invention, the composition is preferably maintained by heating at a temperature greater than its fluidification point. The device used in the context of the process thus preferably comprises a heating and temperature-control unit located at the casting nozzle.

The process of the invention can be carried out on a site for the manufacture of cosmetic products but also at a sales outlet or in a beauty salon.

When the process is carried out in a public place, the consumer can be consulted prior to stage a) in order to choose the functionalities, the form and/or the hue of the cosmetic product which he desires. In this case, he can provide a photograph or a drawing which will be reproduced on a computer before being converted into control data in order to produce the successive deposits.

The invention is illustrated by the following examples. Unless otherwise indicated, the values shown in the context of the present invention result from measurements carried out at 25° C. and at 1 atm ($10^5$ Pa).

EXAMPLE 1

Multihue Lipstick

Preparation of the Compositions

Three compositions of different hues are prepared: a red, a purple and a pink. The three compositions differ in the natures and the relative proportions of the pigments and pearlescent agents. The ingredients of which they are composed, and also their proportions, expressed as percentages by weight, are reproduced hereinafter.

| | |
|---|---|
| Mixture of polyethylene, beeswax and ozokerite | 12.7 |
| Mixture of bentone and $C_{10}$-$C_{30}$ esters | 3.4 |
| Mixture of polyisobutene, esters, polydecene and octyldodecanol | 64.5 |
| Mixture (1) of pigments and pearlescent agents or Mixture (2) of pigments and pearlescent agents or Mixture (3) of pigments and pearlescent agents | 15.9 |
| Preservatives, active agents or fragrances | q.s. for 100 |

The compositions are obtained by mixing the ingredients with stirring at a temperature equal to 95° C. The compositions are cooled to 25° C. The hardness and the dropping points of the compositions are subsequently measured by the following methods.

The hardness of the compositions was measured with a texture analyzer from Stable Micro Systems, TA.XT.Plus model, by penetration of a hemispherical probe having a diameter of 12.7 mm (known as Delrin finger). The measurement was carried out in a 100 ml Cleopatra pot and it was repeated three times.

The parameters of the measurement were as follows:
Approach 2 mm/s
Test 2 mm/s
Withdrawal 2 mm/s
Penetration 13 mm
Relaxation 25 sec
Triggering force 2 g.

The dropping point was measured with a Mettler Toledo DP70 apparatus provided with standardized cups having an orifice diameter of 2.8 mm, by adopting a heat rate of 2.0° C./min, a starting temperature of 40° C. and an end temperature of 95° C. The drop is detected visually using a camera incorporated in the apparatus.

The first composition has a hardness of 43.3 N and a dropping point equal to 78.2° C. The second composition has a hardness of 40.2 N and a dropping point equal to 79.4° C. The third composition has a hardness of 40.7 N and a dropping point equal to 77.5° C.

Casting Device

The casting device comprises a flat noncosmetic support, three nozzles and a feed means for each nozzle. Each nozzle exhibits a circular orifice with a diameter of 0.5 mm; the nozzle is connected to mechanical means which allow it to be displaced along a vertical trajectory. The support is provided with mechanical means which allow it to move in the plane which it defines.

The casting device is placed in a chamber thermostatically controlled at 25° C.; it is connected to a computer which controls the means for feeding the nozzles, the displacement of the nozzles and the displacement of the support, in order to manufacture a lipstick stick comprising three hues exhibiting geometric patterns which have been predefined.

Casting Process

In this process, the compositions are cast by successive deposits according to a predetermined sequence programmed by control software.

The first composition is fluidified at a fluidification temperature of the order of 90-95° C., introduced into the first nozzle by a first feed means and then cast at atmospheric pressure on the support in order to form a first thread of the first composition. The form of the thread deposited is defined by the movement of the support, which may follow a linear or curved trajectory during the casting. The casting of the first deposit or the first composition is halted by computer control of the means for feeding the first nozzle.

The second nozzle and the support will subsequently be positioned so as to produce a first thread of the second composition, under the same conditions as those which were described above for producing the first deposit of the first composition. The casting of the first deposit of the second composition is subsequently halted.

The program for controlling the means for feeding the three nozzles defines the sequence and the durations of casting of the three compositions as a function of the patterns and forms which it is desired to obtain.

For example, the series of following stages can be carried out:

Stage i): casting the first deposit of the first composition and then the first deposit of the second composition on the support, at an unvarying distance between the support and the nozzles, for subsequently Stage ii): increasing the distance between the support and the nozzles by a length equal to the thickness of the first deposits, and casting the first deposit of the third composition, and the second deposit of the first composition, on the deposits produced in the preceding stage, then Stage iii): increasing the distance between the support and the nozzles by a length equal to the thickness of the deposits produced in stage ii), and casting the second deposit of the second composition, and the second deposit of the third composition, on the deposits produced in stage ii), Stage iv): repeating stages i) to iii) while increasing the distance between the support and the nozzles within each stage, so as to keep unvarying, from one stage to the other, the gap between the nozzle and the surface on which the deposits have to be produced.

Once the sequence of stages is terminated, the product consisting of the successive deposits is separated from the support of the device.

Figure 1:
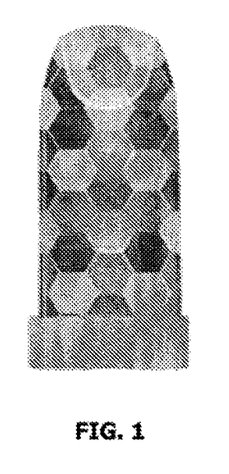
FIG. 1 is a diagrammatic view of a multihue cosmetic product obtained by the process of the invention.

By following this sequence, the product obtained can be a lipstick in the stick form as represented in FIG. 1. This lipstick consists of dodecahedron-shaped domains. The choice of the hues is such that the combination recreates a harmonious and attractive whole.

EXAMPLE 2

Multitexture Lip Balm

Preparation of the Compositions

A transparent composition (1) is prepared according to the same process as that described in example 1. The ingredients of which it is composed, and also their proportions, expressed as percentages by weight, are reproduced hereinafter.

| Phase A | |
|---|---|
| Bis-Dioctadecylamide Dimer Dilinoleic Acid/Ethylenediamine Copolymer | 21 |
| Ethylhexyl Hydroxystearate | 11 |
| Hydrogenated polyisobutene | 56 |
| Phase B | |
| Hydrogenated styrene/methyl styrene/indene copolymer | 10 |
| Cetyl Alcohol | 3.2 |
| Dibutyl Lauroyl Glutamide | 0.4 |
| Dibutyl Ethylhexanoyl Glutamide | 0.4 |

The colored composition (2) is prepared according to the same process as that described in example 1. The ingredients of which it is composed, and also their proportions, expressed as percentages by weight, are reproduced hereinafter.

| | |
|---|---|
| Polyethylene, beeswax and ozokerite wax | 10.2 |
| Bentone, $C_{10}$-$C_{30}$ esters | 25.5 |
| Polyisobutene, esters, polydecene and octyldodecanol | 60.3 |
| Pigments and pearlescent agents | 0.7 |
| Preservatives, active agents or fragrances | q.s. for 100 |

The hardness and the dropping point of the two compositions are measured by the methods used in example 1. The composition (1) has a hardness of 6.4 N and a dropping point equal to 82.8° C. The composition (2) has a hardness of 18.3 N and a fluidification point equal to 75.4° C.

Casting Process

In a first step, at least one deposit of cylindrical form of the transparent composition is produced on the support.

In a second step, cylindrical sections are successively cast, which sections are superimposed and each comprise deposits of the transparent composition (1) and of the colored composition (2).

In a third step, at least one deposit of the transparent composition is produced until a cylinder of the desired height is formed in the continuation of the cylinder obtained in the preceding stage.

Figure 2:
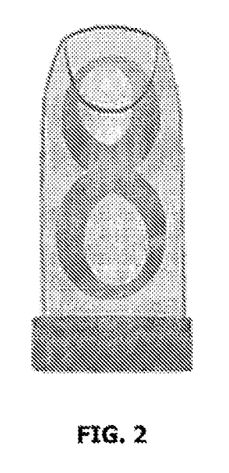
FIG. 2 is a diagrammatic view of a multitexture cosmetic product obtained by the process of the invention.

The product obtained is a lip balm in the form of a stick (FIG. 2). The first transparent composition leaves glimpsed the second colored composition which forms, for example, a Möbius strip. The use of the product makes it possible to deposit, on the lips, a film which is simultaneously glossy, by virtue of the composition (1), and moisturizing, by virtue of the composition (2).

EXAMPLE 3

Multisubstance Foundation

Preparation of a Composition

A composition is prepared according to the same process as that described in example 1. The ingredients of which it is comprised, and also their proportions, expressed as percentages by weight, are reproduced hereinafter.

| | |
|---|---|
| Polyethylene wax | 3 |
| Beeswax | 3 |
| Hydrogenated glycerides | 3.7 |
| Hectorite | 0.8 |
| Esters | 5.45 |
| Oils | 9.7 |
| Liquid sunscreens | 7.5 |
| Pigments | 19 |
| Water | q.s. for 100 |
| Emollients and preservatives | 5.6 |
| Vinyl dimethicone/methicone silsesquioxane crosspolymer, cellulose gum and polymethylsilsesquioxane | 4.6 |
| Solid sunscreens | 1.5 |

The hardness and the dropping point of the two compositions are measured by the methods used in example 1. The composition has a hardness of 12.8 N and a dropping point equal to 58.4° C.

Casting Process

Several successive deposits of the foundation composition are produced according to the process of the invention by using, as support, a three-dimensional object. The deposits are produced so as to cover the surface of the support in its entirety over an unvarying thickness, so that the support is coated and not visible.

The product obtained is a foundation having a fresh and aqueous effect. The cosmetic composition is backed by the support and exhibits the same form. The cosmetic composition can be withdrawn with a brush. The support appears to the user as the composition is withdrawn. The support can be made of thermoplastic polymer and have been fashioned according to a process of casting by successive deposits, or by molding.

The invention claimed is:

1. A casting process for the manufacture of a cosmetic product comprising:
   a) heating a solid composition containing an oil and having a fluidification point ranging from 30 to 150° C. and a mean hardness, as measured at 25° C. using a texture analyzer provided with a hemispherical probe, ranging from 0.5 to 80 N, to a temperature greater than said fluidification point so as to obtain a fluid composition;
   b) introducing the fluid composition into a casting nozzle having an orifice with a diameter ranging from 0.01 to 5 mm;
   c1) casting the fluid composition through the orifice at a casting temperature and at a casting flow rate ranging from 0.05 to 2 mm³/s, obtaining an ejected volume of fluid composition, dropping said ejected volume to a support thereby cooling said ejected volume to 25° C. and forming a solid deposit of the composition on said support, the solid deposit essentially retaining the form of the ejected volume at the orifice;
   c2) changing the nozzle position with respect to the support and moving the nozzle in at least one of the three space directions;
   d) halting the casting of the fluid composition, then optionally
   e) changing the nozzle position with respect to the support, and
   f) repeating a) to e) above at least one time with said composition or with another composition, wherein the other composition contains an oil, has a fluidification point ranging from 30 to 150° C., and has a mean hardness, measured at 25° C. using a texture analyzer provided with a hemispherical probe, ranging from 0.5 to 80 N, and
   wherein the support does not act as a container for the volume of the fluid composition, and
   the solid deposit has essentially the form of a sphere having a diameter ranging from 0.01 to 1 mm.

2. The casting process as claimed in claim 1, wherein the casting temperature is less than or equal to the fluidification temperature.

3. The process as claimed in claim 1, wherein the form of the ejected volume is identical to the form of the solid deposit, in the absence of any external mechanical or thermal stress applied to the solid deposit.

4. The process as claimed in claim 1, wherein the mean diameter of the solid deposits is equal to the diameter of the nozzle orifice.

5. The process as claimed in claim 1, wherein the dynamic viscosity of the fluid composition at the casting temperature and atmospheric pressure ranges from 1 to 10000 mPa·s.

6. The process as claimed in claim 1, wherein the fluidification temperature is in a range from 1 to 15° C. higher than the fluidification point of the composition.

7. The process as claimed in claim 1, wherein the solid composition has a dropping point of greater than 50° C.

8. The process as claimed in claim 1, wherein the support is a cosmetic support.

9. The process as claimed in claim 1, further comprising a step g) of casting a thermoplastic substance, wherein step g) is carried out prior to, subsequent to or at the same time as step c1).

10. The process as claimed in claim 1, wherein the dynamic viscosity of the fluid composition at the casting temperature and atmospheric pressure ranges from 100 to 500 mPa·s.

11. The process as claimed in claim 1, wherein the solid composition has a dropping point ranging from 70° C. to 85° C.

12. The process as claimed in claim 1, wherein the solid deposits are not deformed by mechanical or thermal stress subsequent to their formation on the support.

13. The process according to claim 1, wherein the solid deposits are in contact together and are arranged nonrandomly.

14. The process according to claim 1, wherein the solid composition comprises from 55 to 65% by weight of the solid composition of one or more oils, from 5 to 11% by weight of the solid composition of one or more waxes, from 10 to 30% by weight of the solid composition of one or more pasty fatty substances, and a mixture of one or more pigments and one or more fillers.

15. The process according to claim 1, wherein the cosmetic product is a multihue, multitexture or multisubstance product.

16. The process according to claim 1, wherein the cosmetic product is chosen from the group consisting of a makeup product, a care product, a sun protection product and a scenting product.

17. The process according to claim 1, wherein the cosmetic product is a product for making up lips.

\* \* \* \* \*